United States Patent [19]

Briggs

[11] 4,413,150

[45] Nov. 1, 1983

[54] TWO PRODUCT PROCESS FOR METHYL TERTIARY BUTYL ETHER PRODUCTION

[75] Inventor: Bruce A. Briggs, Wheeling, Ill.

[73] Assignee: UOP Inc., Des Plaines, Ill.

[21] Appl. No.: 332,381

[22] Filed: Dec. 18, 1981

[51] Int. Cl.$^3$ .............................................. C07C 41/05
[52] U.S. Cl. ...................................... 568/697; 44/56; 44/77; 203/DIG. 13
[58] Field of Search ............... 568/697; 203/DIG. 13; 44/77, 56

[56] References Cited

U.S. PATENT DOCUMENTS

| | | | |
|---|---|---|---|
| 2,720,547 | 10/1955 | Wolff et al. | 260/614 |
| 4,182,913 | 1/1980 | Takezono et al. | 568/697 |
| 4,193,770 | 3/1980 | Chase et al. | 568/697 |
| 4,219,678 | 8/1980 | Obenaus et al. | 568/697 |
| 4,252,541 | 2/1981 | Herbstman | 44/56 |
| 4,282,389 | 8/1981 | Droste et al. | 568/697 |
| 4,310,710 | 1/1982 | Torck et al. | 568/697 |

FOREIGN PATENT DOCUMENTS 2047706 12/1980 United Kingdom .

OTHER PUBLICATIONS

Chemical & Engineering News, Jun. 25, 1979, pp. 35–36 by Stephen C. Stinson entitled "New Plants, Processes Set for Octane Booster".

Paper presented at AIChE 85th National Meeting, Jun. 4–8, 1978 by Fritz Obenaus & Wilhelm Droste, entitled "Huls-Process: Methyl Tertiary Butylether".

*Primary Examiner*—Howard T. Mars
*Attorney, Agent, or Firm*—James R. Hoatson, Jr.; John F. Spears, Jr.; William H. Page, II

[57] ABSTRACT

A hydrocarbon conversion process which net high purity isobutane feed streams into two product streams containing an ether such as methyl tertiary butyl ether (MTBE) by reaction with methanol or ethanol. The isobutylene, alcohol and a recycle stream containing $C_4$ hydrocarbons, alcohol and the product ether are passed through an etherification zone. The total etherification zone effluent stream is separated in a single fractionation column. Preferably the new overhead of the fractionation column is divided into the recycle stream and a second portion which is combined with a portion of the bottoms of this column to produce a gasoline grade MTBE product stream. The remainder of the fractionation column bottoms is a second product stream of chemical grade MTBE.

9 Claims, 1 Drawing Figure

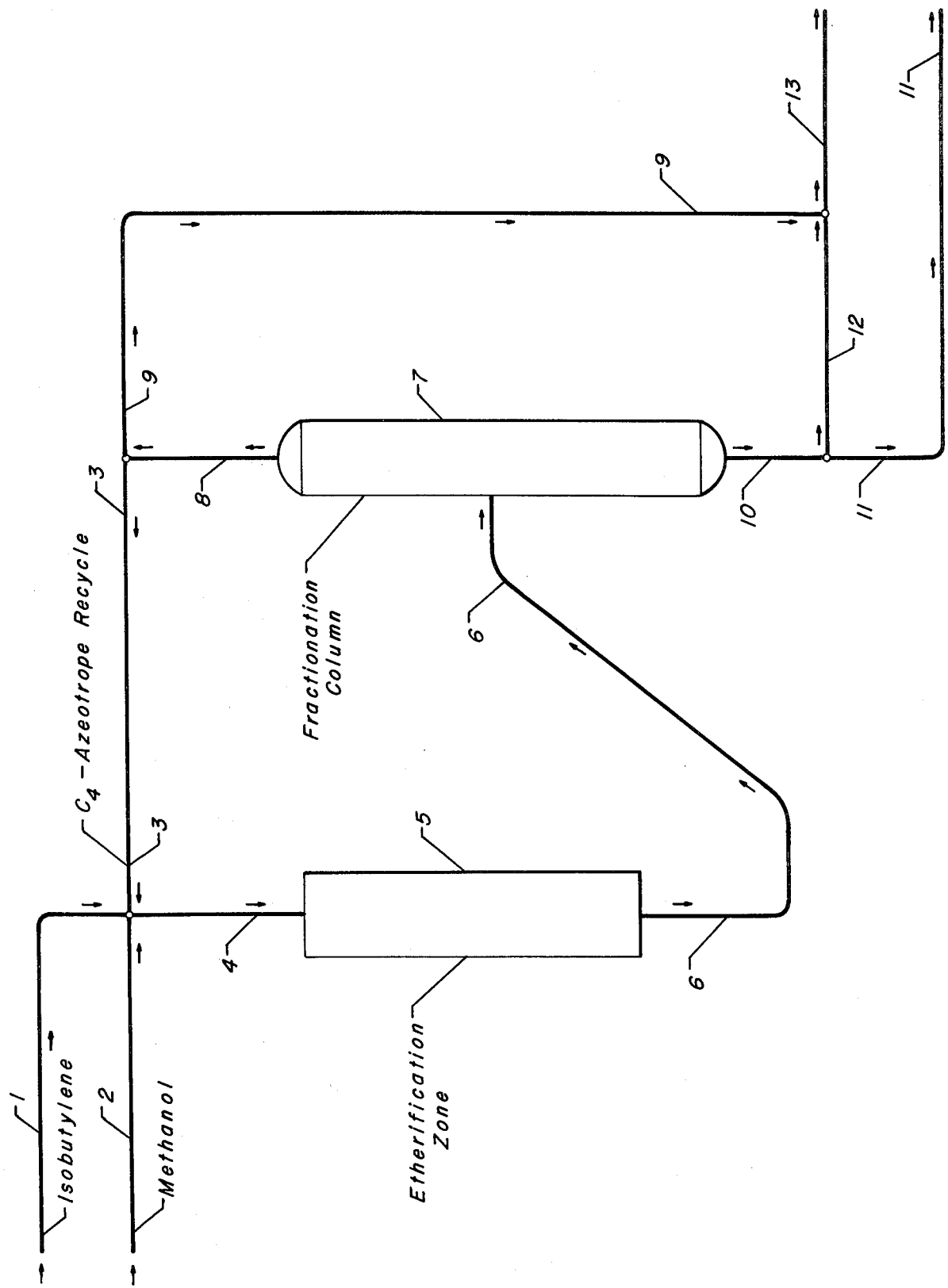

TWO PRODUCT PROCESS FOR METHYL TERTIARY BUTYL ETHER PRODUCTION

FIELD OF THE INVENTION

The invention is a hydrocarbon conversion process in which isobutylene is converted to both chemical grade and gasoline grade methyl tertiary butyl ether (MTBE) which are removed as separate product streams. The invention more directly relates to a process, which may also be referred to as an etherification process, in which high purity isobutylene is reacted with methanol. The invention specifically relates to the fractionation and recycle methods employed in such a process to obtain high isobutylene conversion with a minimum amount of equipment.

PRIOR ART

The production of ethers by the reaction of an isoolefin with an alcohol is well known and is practiced commercially. This highly selective reaction is also used to remove isoolefins, especially isobutylene, from mixed hydrocarbon streams such as the $C_4$ streams produced in steam cracking plants which produce ethylene. Increased attention has been focused on ether production due to the rapidly increasing demand for lead-free octane boosters for gasoline such as MTBE. A detailed description of processes, including catalysts, processing conditions and product recovery, for the production of MTBE from isobutylene and methanol are provided in U.S. Pat. Nos. 2,720,547 and 4,219,678 (Cl. 268-697) and in an article at page 35 of the June 25, 1979 edition of *Chemical and Engineering News*. The preferred reactor system is described in a paper presented at the American Institute of Chemical Engineers 85th National meeting on June 4–8, 1978 by F. Obenaus et al. This paper shows that the process may be used to produce any of three different purity MTBE product streams.

Three other recent references which are relevant for their showing of the state of the art of MTBE production from isobutylene are U.S. Pat. Nos. 4,252,541 (Cl. 44-56) and 4,282,389 (Cl. 568-697) and British Patent application No. 2,047,706A. U.S. Pat. No. 4,182,913 also shows an etherification process for MTBE production, with the overhead of a flash column which receives the etherification reaction zone effluent stream being recycled by admixture with the feed streams. The methanol-MTBE mixture removed from the bottom of the flash column is described as a suitable gasoline additive, and the use of a high purity isobutylene feed stream is also disclosed.

BRIEF SUMMARY OF THE INVENTION

The invention provides a process for the conversion of isobutylene to methyl tertiary butyl ether or another ether which achieves a high isobutylene conversion rate at a very low capital cost. The low capital cost results from eliminating the multiple fractionation columns used in the prior art and by accepting the simultaneous production of a lower purity MTBE stream, which despite its decreased purity is an ideal gasoline antiknock additive.

One embodiment of the invention may be broadly characterized as a hydrocarbon conversion process which comprises the steps of reacting isobutylene with a $C_1$ to $C_3$ aliphatic alcohol in an etherification zone and producing an etherification zone effluent stream which comprises $C_4$ hydrocarbons, the alcohol and a reaction product ether; separating the entire etherification zone effluent stream in a single fractionation column into a new overhead stream comprising $C_4$ hydrocarbons, the alcohol and the ether and a net bottoms stream comprising the ether and which is substantially free of $C_4$ hydrocarbons and the alcohol; passing a first portion of said net overhead stream into the etherification zone as a recycle stream; admixing a second portion of said net overhead stream with a first portion of said net bottoms stream to form a first product stream of medium grade ether; and, removing a second portion of said net bottoms stream as a second product stream of chemical grade ether.

BRIEF DESCRIPTION OF THE DRAWING

The Drawing is a very simplified flow diagram of the preferred embodiment of the invention.

A first feed stream of high purity isobutyene enters the process through line 1 and is combined with a second feed stream comprising methanol which enters the process through line 2. A recycle stream which comprises both $C_4$ hydrocarbons and an azeotrope-derived mixture of MTBE and methanol which is carried by line 3 joins the two feed streams and is carried by line 4 into an etherification zone 5. This zone will normally comprise two different reactors in series flow but is represented by a single vessel in the Drawing. The etherification zone effluent stream carried by line 6 comprises an admixture of the product MTBE, excess methanol, reaction by-products such as tertiary butyl alcohol, a significant amount of isobutylene and various amounts of other $C_4$ hydrocarbons including normal butenes, butadiene and isobutanes and normal butanes.

The etherification zone effluent stream is passed into an intermediate point of a single fractionation column 7. The etherification zone effluent stream is therein separated into a net overhead stream carried by line 8 and a net bottoms stream carried by line 10. The net bottoms stream comprises high purity MTBE and is substantially free of any $C_4$ hydrocarbon or methanol. The net overhead stream of the fractionation column 7 comprises a mixture of substantially all the $C_4$ hydrocarbons and methanol contained in the etherification zone effluent stream and also contains a sizable amount of MTBE. The overhead stream is divided into two portions of equal composition with a larger first portion being recycled through line 3 to the etherification zone to return isobutylene to the reaction zone. A smaller portion of the overhead stream which may be on the order of from about 5 to about 25 volume percent of the total net overhead stream is passed through line 9 and combined with a first portion of the net bottoms stream carried by line 12 to produce a gasoline grade MTBE product stream removed from the process through line 13. A second portion of the net bottoms stream of the fractionation column is removed from the process through line 11 as the second product stream of higher purity or chemical grade MTBE.

DETAILED DESCRIPTION

Large scale commercial plants for converting isobutylene into methyl tertiary butyl ether (MTBE) by etherification with methanol are now in operation. Additional commercial facilities to produce MTBE are being designed and built. A sizable amount of the MTBE produced in these plants is destined to be utilized as antiknock additives in lead-free gasolines. However, plans have also been announced for the production of very high purity isobutylene for use in the manufacture of polyisobutylenes and tert-butyl-phenol by cracking MTBE into isobutylene and methanol. Processes for converting isobutylene into MTBE therefore have a sizable utility in the chemical processing industries.

It is an objective of the subject invention to provide a low capital cost process for the conversion of isobutylene into MTBE. It is another objective of the subject invention to provide a process for producing ethers such as MTBE which is practical for small to intermediate size units in petroleum refineries having an existing source of relatively high purity isobutylene. It is a further objective of the subject invention to provide a process which reduces the capital and utility costs of producing MTBE and other ethers.

There are two feed materials to the subject process. One of the feed materials is a water-soluble alcohol which preferably has less than four carbon atoms per molecule. This alcohol is preferably methanol, with ethanol being the next preferred. The alcohol can however be chosen from primary and secondary propanol, the various propanols, the dihydroxy alcohols such as ethylene glycol and propylene glycol and other alcohols. The preferred class of alcohols are $C_4$-minus aliphatic monohydroxy alcohols. The majority of the description of the invention is presented in terms of the reaction of isobutylene with methanol since these are the preferred feed materials and this is the commercially predominant reaction. However, it is not intended to thereby lessen the scope of the inventive concept. This is especially true since there have been predictions that the expected large demand for ethers as antiknock additives will lead to the use of large amounts of ethanol produced by fermentation or by Fischer-Tropsch synthesis.

It is very much preferred that the second feed material is isobutylene although the subject process could be performed with isopentene as the second feed material. The second feed material must enter the process as a high purity stream, a term which is intended to refer to an isoolefin concentration above 85 mole percent. Preferably, this feed stream contains over 90 mole percent isoolefin, and it is very much preferred that the isoolefin feed stream comprises at least 93 mole percent isobutylene.

The etherification reaction between isobutylene and methanol is very specific. Essentially none of any other $C_4$ hydrocarbon, such as isobutane or normal butene, present in an isobutylene feed stream reacts with the methanol. An etherification process unit is therefore a very efficient means of extracting isobutylene from a stream of mixed $C_4$ hydrocarbons. If desired the isobutylene can then be recovered by cracking the MTBE into high purity isobutylene and methanol which can be recycled. The high selectivity of the etherification reaction allows the use of mixed $C_4$ streams as the isoolefin feed stream rather than requiring expensive purification of the isobutylene. This allows the use of many readily available $C_4$ streams as an etherification zone feedstock and greatly increases the commercial feasibility of the process. However, as previously stated the subject process is most feasible with a high purity isoolefin feed stream.

The unreactive components of the isoolefin feed stream leave the etherification zone as part of the etherification zone effluent stream. It is preferred that these unreactive compounds, $C_4$ hydrocarbons to be specific, comprise less than 20 mole percent of the etherification zone effluent stream. They must be separated from any etherification product as part of a product recovery step. The separation of these light components from the much higher boiling etherification products is normally quite easy due to the greatly different boiling points of these materials. However, it is customary to have an excess of the alcohol present in the reaction zone to help obtain a high level of isoolefin conversion. This alcohol is also present in the etherification zone effluent stream and usually complicates the recovery of the product ether. In the specific case of MTBE production, the problems arise because methanol and MTBE form an azeotropic mixture at the conditions and concentrations normally employed to separate an MTBE unit effluent stream by fractional distillation.

Several approaches to this problem of etherification zone effluent separation have been conceived and are described in the previously referred to prior art. The preferred method of separating pure MTBE from the effluent of an etherification zone is described in U.S. Pat. No. 4,219,678 which was cited above. In this method the unreacted $C_4$ hydrocarbons are removed overhead in a first fractionation column and removed from the process. The bottoms of the first column are passed into a second fractionation column and therein separated into a net bottoms stream of pure MTBE and the methanol-MTBE azeotrope. This azeotrope is then recycled to the reaction zone. If a lower purity MTBE product is desired, the bottoms product of the first fractionation column, or even the etherification zone effluent itself, may be withdrawn as the product. However, to obtain MTBE at greater than 98.0 weight percent purity by the prior art methods, it is necessary to employ two fractionation columns.

The subject invention allows the production of very high purity or chemical grade MTBE (99.2% plus) with only one fractionation column. This significantly reduces the capital and utilities cost of the process since the overall etherification zone is relatively straightforward. That is, a second fractionation column is a significant increase in plant equipment compared to a process which only has two or three reactors and one fractionation column. Besides the column itself, it is also necessary to procure the overhead condenser and reboiler, which are major expense items, pumps, controllers, safety systems, etc. The additional column also requires operating the additional overhead condenser and reboiler which increase heating and cooling costs of the process. The simplicity of the subject invention therefore effects a sizable reduction in initial investment and operating costs and may make the difference in whether a proposed MTBE unit is economically affordable.

Several suitable etherification processes have been described in the available literature, with these processes being presently used to produce MTBE for petrochemical and gasoline additive consumption. The preferred form of the etherification zone is similar to that described in U.S. Pat. No. 4,219,678 and shown in the previously cited paper. In this instance the isobutane or other isoolefin, methanol or other feed alcohol, and a recycle stream containing the product ether and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites and various sulfonated resins. The use of a sulfonated solid resin catalyst is preferred. These resin-type catalysts include the reaction products of phenol-formaldehye resins and sulfuric acid and sulfonated polystyrene resins including those cross-linked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions includes a superatmospheric pressure sufficient to maintain the reactants as a liquid phase, generally below about 200 psig, and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with an etherification zone comprising two or more separate reactors. As described in the references the first reactor and possibly the second reactor are of the multi-tube type in which the reactants pass through small diameter reaction tubes surrounded by heat exchange media. The final reactor is preferably of the fixed bed type.

The mole ratio of total feed alcohol to total isoolefin entering the reaction zone should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided. It is preferred that the recycle rate of the hereinafter described overhead recycle stream is adjusted to provide a total methanol to isobutylene mole ratio between about 1.15:1.0 and 1.25:1.0. Depending on the economics of various operating and design factors a recycle to fresh feed weight ratio in the area of 0.5 could be employed to maintain the desired methanol to isobutylene ratio.

The etherification zone effluent stream is passed into an intermediate point of a single fractionation column. A properly designed and operated column to perform the desired separations may comprise a column having about 50 trays. This column could be operated with a bottoms liquid temperature of about 160° C. at a pressure of approximately 12 psig. The bottoms stream of the fractionation column should be high purity chemical grade MTBE, although the purity of the bottoms product can be adjusted as desired. The overhead stream of the column should contain substantially all of the components of the etherification zone effluent stream other than the product ether. As used herein the term "substantially all" is intended to indicate at least 90 and preferably at least 95 mole percent of a specified chemical compound or class of compounds. The overhead stream of the fractionation column will therefore contain at least 90 mole percent of the $C_4$ hydrocarbons, including unreacted isobutylene, present in the effluent stream and also as least 90 mole percent of the methanol or other alcohol contained in the effluent stream. The overhead stream will also contain a significant amount of the product ether, which in the case of MTBE is tied up in a methanol-MTBE-$C_4$ hydrocarbon azeotropic mixture. The MTBE content of this mixture may be reduced by increasing the pressure within the column as described in the cited references.

The net overhead stream of the single fractionation column is divided into two portions of identical composition. A larger first portion of the overhead stream is passed into the etherification zone as a recycle stream to recover isobutylene and methanol, with the recycled methanol aiding in achieving the desired high isobutylene conversions. A smaller second portion of the net overhead stream is combined with a portion of the column bottoms stream to produce a gasoline grade MTBE stream. The methanol contained in the overhead stream is also a high octane number material and is an entirely acceptable if not desired gasoline component. The $C_4$ hydrocarbons may be used as a substitute for butanes blended into gasoline and hence do not constitute an impurity in gasoline. The second portion of the net overhead stream may be between 5 and 40 weight percent of the total net overhead stream depending on such factors as the purity of the isoolefin feed stream and the desired quantity of gasoline grade ethers. However, it is preferred that the second portion of the net overhead stream equals between 10 and 30 weight percent of the entire net overhead stream. The first portion of the net overhead stream is therefore preferably equal to between about 70 to 90 weight percent of the net overhead stream.

To ensure a proper understanding of the subject process the following projected summary mass balance is presented for a commercial scale unit to be operated at the previously specified conditions and designed in accordance with the other preferences set out herein. The isoolefin feed stream to this unit has a flow rate of about 32,350 kg/hr (kilograms per hour) and contains 96.1 weight percent isobutylene. The isoolefin feed stream is produced by superfractionation, but could also be produced through the use of a selective solid absorbent. The feed stream contains about 540 kg/hr of isobutane, 31,100 kg/hr of isobutylene, 440 kg/hr of n-butane, 150 kg/hr of butene-2, 80 kg/hr of butene-1 and 30 kg/hr of butadiene. These components will vary with the source of the isobutylene feed stream and the operation of the separation facilities. Also fed to the single stage etherification zone is the alcohol feed stream containing about 18,560 kg/hr of methanol and 20 kg/hr of water. A recycle stream characterized below and having a flow rate of approximately 14,750 kg/hr is also passed into the etherification zone. The inlet temperature to the first water cooled reactor is about 55° C. and the outlet temperature from the last reactor is about 46° C.

The per pass isobutylene conversion in the etherification zone is approximately 97.8 percent. The overall conversion of isobutylene is 99 percent since isobutylene is recycled. The ability to obtain this high overall conversion with a single stage etherification reactor is another advantage of the subject process since a two stage etherification zone (one employing intermediate MTBE removal by fractionation) would normally be required to achieve this level of conversion.

The entire effluent of the etherification zone is passed into a single fractionation column and divided into a net overhead stream and a net bottoms stream. The total net overhead stream has a flow rate near 18,430 kg/hr. The flow rates of the individual components of the overhead stream include about 2,690 kg/hr. of water, about 6,530 kg/hr of MTBE, 4,150 kg/hr of methanol, 2,220 kg/hr of normal butane, 2,690 kg/hr of isobutane, 1,560 kg/hr of isobutylene, 1,150 kg/hr of normal butenes and 140 kg/hr of butadiene. This overhead stream is split into the larger first portion which becomes the previously referred to recycle stream and a smaller second portion which serves as a drag stream to prevent the buildup of $C_4$ hydrocarbons and reaction by-products within the process. The net bottoms stream of the fractionation column has a total flow rate of approximately 47,240 kg/hr. Of this flow about 190 kg/hr is methanol, 80 kg/hr is tertiary butyl alcohol (TBA) and 25 kg/hr is diisobutylenes. Approximately 46,950 kg/hr of the bottoms stream is MTBE. The bottoms stream is also divided into two portions, with a first portion of the net bottoms stream being admixed with the smaller second portion of the net overhead stream. The admixture of these two streams produces a product stream of gasoline grade MTBE containing about 90.8 weight percent MTBE. The total flow rate of this product stream is about 27,280 kg/hr. The remaining portion of the net bottoms stream is removed as a second product stream containing about 99.2 weight percent MTBE and having a flow rate of approximately 23,654 kg/hr. This product stream contains a total of about 0.15 weight percent of various $C_4$ hydrocarbons.

The invention may be characterized as a hydrocarbon conversion process which comprises the steps of passing the first feed stream comprising at least 85 mole percent isobutylene and a small amount of other $C_4$ hydrocarbons, a recycle stream comprising methanol, methyl tertiary butyl ether and $C_4$ hydrocarbons and a second feed stream comprising methanol into an etherification zone operated at etherification conditions and thereby producing an etherification zone effluent stream which comprises methanol, $C_4$ hydrocarbons and methyl tertiary butyl ether; separating the etherification zone effluent stream in a fractionation column into a net bottoms stream which comprises methyl tertiary butyl ether and a net overhead stream which comprises substantially all of the methanol and isobutane present in the etherification zone effluent stream and which also comprises methyl tertiary butyl ether; passing a first portion of said net overhead stream into the etherification zone as the previously referred to recycle stream; combining a second portion of said net overhead stream with a first portion of said net bottoms stream and thereby forming a first product stream comprising methanol and methyl tertiary butyl ether; and removing a second portion of said net bottoms stream as a second product stream containing a higher concentration of methyl tertiary butyl ether than the first product stream.

I claim as my invention:

1. A hydrocarbon conversion process which comprises the steps of:
   (a) reacting isobutylene with a $C_1$ to $C_3$ aliphatic alcohol in an etherification zone and producing an etherification zone effluent stream which comprises $C_4$ hydrocarbons, unconverted alcohol and a reaction product ether;
   (b) separating the entire etherification zone effluent stream in a single fractionation column into a net overhead stream comprising $C_4$ hydrocarbons, the unconverted alcohol and a portion of the reaction product ether and a net bottoms stream comprising the remainder of the reaction product ether and which is substantially free of the alcohol;
   (c) passing between about 70 to 90 weight percent of said net overhead stream into the etherification zone;
   (d) admixing between 5 to 40 weight percent of said net overhead stream with a first portion of said net bottoms stream to form a first product stream; and,
   (e) removing a second portion of said net bottoms stream as a second product stream.

2. The process of claim 2 further characterized in that the etherification zone effluent stream contains less than 10 mole percent $C_4$ hydrocarbons.

3. The process of claim 2 further characterized in that the alcohol is ethanol.

4. The process of claim 2 further characterized in that the alcohol is methanol.

5. The process of claim 4 further characterized in that the mole ratio of methanol to isobutylene which enters the etherification zone is greater than 1.15:1.0.

6. A hydrocarbon conversion process which comprises the steps of:
   (a) passing a first feed stream comprising at least 85 mole percent isobutylene and a small amount of other $C_4$ hydrocarbons, a recycle stream comprising methanol, methyl tertiary butyl ether and $C_4$ hydrocarbons and a second feed stream comprising methanol into an etherification zone operated at etherification conditions and thereby producing an etherification zone effluent stream which comprises methanol, $C_4$ hydrocarbons and methyl tertiary butyl ether;
   (b) separating the etherification zone effluent stream in a fractionation column into a net bottoms stream which comprises methyl tertiary butyl ether and a net overhead stream which comprises substantially all of the methanol and isobutane present in the etherification zone effluent stream and which also comprises methyl tertiary butyl ether;
   (c) passing between about 70 to 90 weight percent of said net overhead stream into the etherification zone as the previously referred to recycle stream;
   (d) combining between 5 to 40 weight percent of said net overhead stream with a first portion of said net bottoms stream and thereby forming a first product stream comprising methanol and methyl tertiary butyl ether; and
   (e) removing a second portion of said net bottoms stream as a second product stream containing a higher concentration of methyl tertiary butyl ether than the first product stream.

7. The process of claim 6 further characterized in that the first feed stream comprises at least 93 mole percent isobutylene.

8. The process of claim 7 further characterized in that the etherification zone effluent stream contains less than 20 mole percent $C_4$ hydrocarbons.

9. The process of claim 6 further characterized in that the flow rate of the second portion of said net overhead stream is between about 10 and about 30 weight percent of said net overhead stream.

* * * * *